US009020092B2

(12) United States Patent
Wang et al.

(10) Patent No.: US 9,020,092 B2
(45) Date of Patent: Apr. 28, 2015

(54) APPARATUS AND METHOD FOR ANGULAR RESPONSE CALIBRATION OF PHOTON-COUNTING DETECTORS IN SPARSE SPECTRAL COMPUTED TOMOGRAPHY IMAGING

(71) Applicants: Kabushiki Kaisha Toshiba, Minato-ku (JP); Toshiba Medical Systems Corporation, Otawara-shi (JP)

(72) Inventors: Xiaolan Wang, Buffalo Grove, IL (US); Yu Zou, Naperville, IL (US)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 278 days.

(21) Appl. No.: 13/770,829

(22) Filed: Feb. 19, 2013

(65) Prior Publication Data
US 2014/0233694 A1 Aug. 21, 2014

(51) Int. Cl.
G01T 7/00 (2006.01)
A61B 6/03 (2006.01)
A61B 6/00 (2006.01)
G06T 11/00 (2006.01)
G01T 1/29 (2006.01)

(52) U.S. Cl.
CPC .............. G01T 7/005 (2013.01); A61B 6/032 (2013.01); A61B 6/488 (2013.01); A61B 6/5294 (2013.01); G06T 11/005 (2013.01); G01T 1/2907 (2013.01); A61B 6/582 (2013.01); A61B 6/4233 (2013.01); A61B 6/4241 (2013.01); A61B 6/482 (2013.01); A61B 6/583 (2013.01)

(58) Field of Classification Search
CPC ...... A61B 6/42; A61B 6/4208; A61B 6/4241; A61B 6/4266; A61B 6/48; A61B 6/482; A61B 6/488; A61B 6/5211; A61B 6/52; A61B 6/5294; A61B 6/58; A61B 6/582; A61B 6/583; A61B 6/032; G01N 23/06; G01N 23/08; G01N 23/083; G01N 23/087; G01T 1/18; G01T 1/20; G01T 1/24; G01T 1/29; G01T 1/2992; G01T 1/36; G01T 1/365; G01T 1/366; G06T 1/00; G06T 1/007; G06T 11/003; G06T 11/005; G06T 11/006; G06T 11/008; G06T 19/00; G06T 19/20; G06T 2207/10072; G06T 2207/10081; G06T 2207/20; G06T 2211/00; G06T 2211/04
See application file for complete search history.

(56) References Cited

U.S. PATENT DOCUMENTS

2014/0233693 A1* 8/2014 Wang et al. ................ 378/5

* cited by examiner

Primary Examiner — Anastasia Midkiff
(74) Attorney, Agent, or Firm — Oblon, McClelland, Maier & Neustadt, L.L.P.

(57) ABSTRACT

A method for detector angular response calibration in computed-tomography (CT) comprising capturing incident X-ray photons, emitted from an X-ray source, via a plurality of energy-discriminating detectors, determining photon counts of the captured incident X-ray photons in a plurality of energy windows at each energy-discriminating detector, and adjusting the photon counts based on a pre-determined detector angular response calibration look-up table for a given view for each energy-discriminating detector at each energy window.

12 Claims, 10 Drawing Sheets

APPARATUS AND METHOD FOR ANGULAR RESPONSE CALIBRATION OF PHOTON-COUNTING DETECTORS IN SPARSE SPECTRAL COMPUTED TOMOGRAPHY IMAGING

FIELD

Embodiments disclosed herein generally relate to computed tomography (CT). In particular, embodiments disclosed herein relate to an apparatus and method for angular response calibration of photon-counting detectors in sparse spectral CT imaging.

BACKGROUND

X-ray tomographic imaging, in its simplest expression, is an X-ray beam traversing an object, and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low-energy X-ray from the generator, the details of the geometry and characteristics of the detector, and the capacity of the acquisition system, are all elements that affect how the actual reconstruction is performed.

In one of many possible geometries, the X-ray source on top of the graph shown in FIG. 1 is emitting an X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Thus, the entire X-ray generator and detector assembly will rotate around the patient. Mathematical considerations show that the tomographic conditions are met when a scan of 180 degrees plus the fan angle is performed.

Conventional X-ray detectors integrate the total electrical current produced in a radiation sensor and disregard the amplitude information from individual photon-detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon-counting and individual pulse height analysis may be used. These X-ray detectors are made possible by the availability of fast semiconductor radiation sensor materials with room-temperature operation and good energy resolution, combined with application-specific integrated circuits (ASICs) suitable for multi-pixel parallel readout and fast counting.

One major advantage of such photon-counting detectors is that, when combined with pulse-height analysis readout, spectral information can be obtained about the attenuation coefficient in the object. A conventional CT detector measures the attenuation at one average energy only, while in reality, the attenuation coefficient strongly depends on the photon energy. In contrast, with pulse-height analysis, the system is able to categorize the incident X-ray photons into several energy bins based on their detected energy. This spectral information can effectively improve material discrimination and target contrast, all of which can be traded for a dose reduction to a patient.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
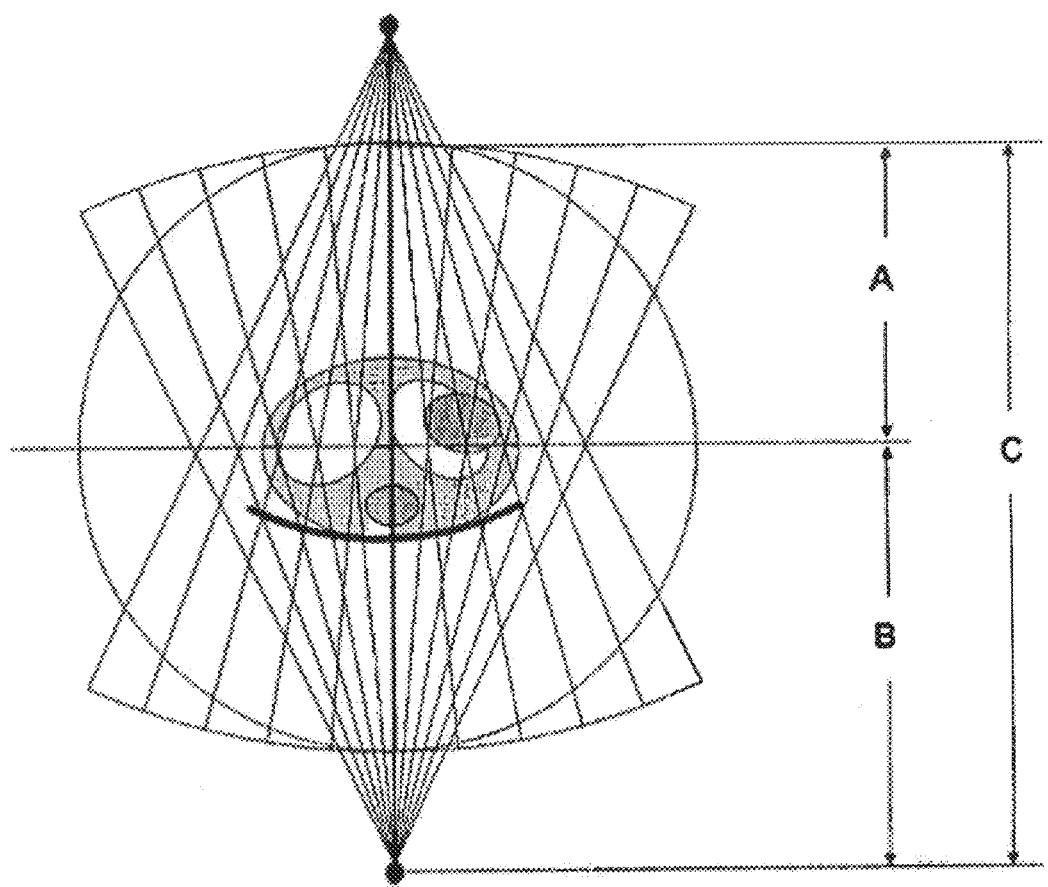
FIG. 1 illustrates an X-ray source emitting an X-ray beam forming a fan, traversing an object.

Embodiments disclosed herein relate to an apparatus and method for angular response calibration of photon-counting detectors in sparse spectral CT imaging.

In one embodiment, there is provided a method for detector angular response calibration in computed-tomography (CT), the method comprising: (1) capturing incident X-ray photons, emitted from an X-ray source at a given view using pre-determined scan parameters, via a plurality of energy-discriminating detectors; (2) determining photon counts of the captured incident X-ray photons in a plurality of energy windows at each energy-discriminating detector; and (3) adjusting the photon counts in each of the plurality of energy windows at each energy-discriminating detector based on a pre-determined detector angular response calibration look-up table.

In one embodiment, there is provided a computed-tomography (CT) apparatus, comprising: (1) a plurality of energy-discriminating detectors configured to capture incident X-ray photons emitted from an X-ray source at a given view using pre-determined scan parameters; and (2) a processor configured to determine photon counts of the captured incident X-ray photons in a plurality of energy windows at each energy-discriminating detector; and adjust the photon counts in each of the plurality of energy windows at each energy-discriminating detector based on a pre-determined detector angular response calibration look-up table.

In one embodiment, there is provided a method to determine a detector angular response calibration look-up table to calibrate angular responses of a plurality of energy-discriminating detectors in a computed-tomography (CT) apparatus, the method comprising: (1) determining an initial detection efficiency parameter value for each of a plurality of combinations of incident angle and energy level by simulating a pre-determined number of single-energy photons at each combination of incident angle and energy level; (2) calculating an incident spectrum on each energy-discriminating detector for each of a plurality of combinations of pre-determined scan parameters, energy level, and pre-determined patient attenuation parameters; (3) performing a set of calibration scans using the plurality of combinations of pre-determined scan parameters with a phantom arranged within the CT apparatus, the phantom corresponding to the pre-determined patient attenuation parameters; (4) measuring detected counts for each energy window at each energy-discriminating detector for each combination of pre-determined scan parameters and the pre-determined patient attenuation parameters; (5) determining a detection efficiency parameter value corresponding to each energy window of each energy-discriminating detector, each combination of pre-determined scan parameters, and the pre-determined patient attenuation parameters, based on the initial detection efficiency parameter value, the incident spectrum, and the detected counts; and (6) determining the detector angular response calibration look-up table based on the determined detection efficiency parameter values corresponding to each energy window of each energy-discriminating detector, the pre-determined scan parameters, and the pre-determined patient attenuation parameters.

Figure 2:
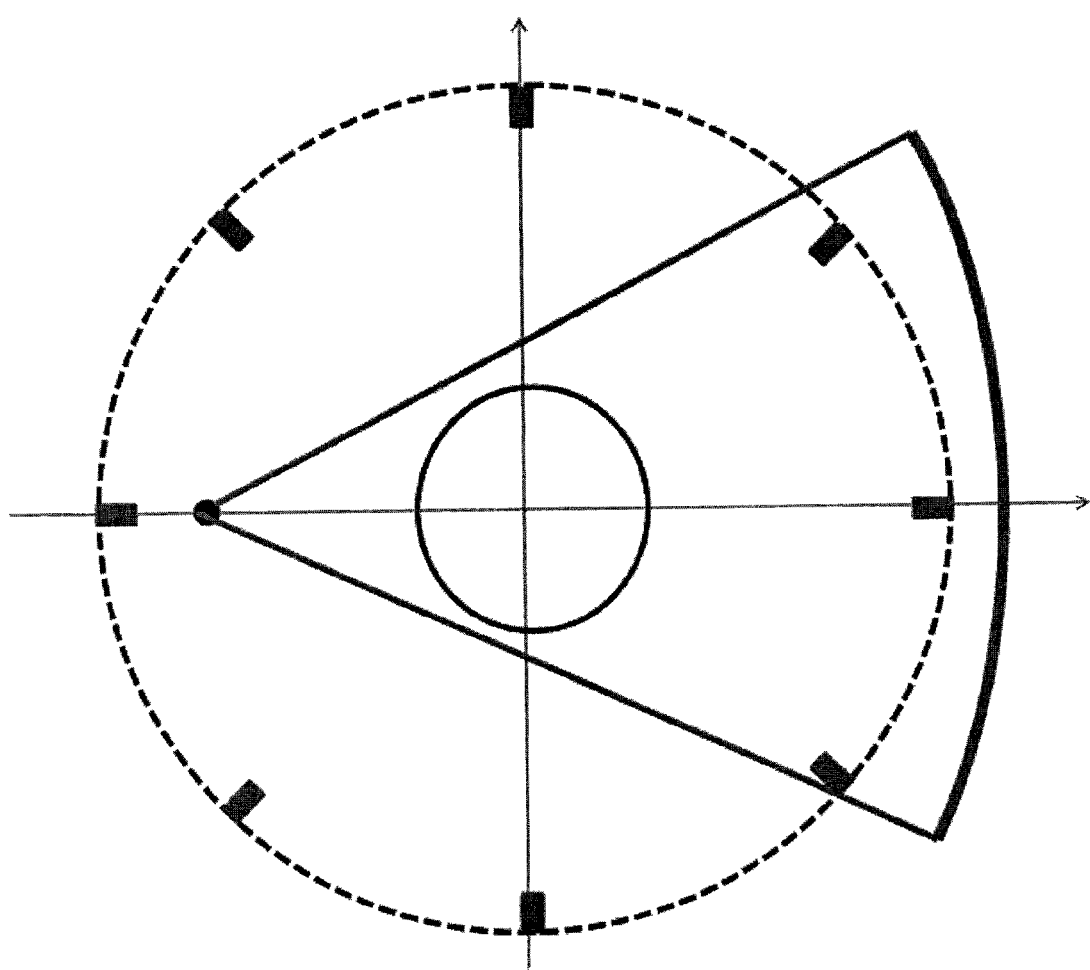
FIG. 2 illustrates a spectral CT imaging system with fixed, sparse photon-counting detectors.

In another embodiment, there is provided an apparatus to determine a detector angular response calibration look-up table to calibrate angular responses of a plurality of energy-discriminating detectors in a computed-tomography (CT) apparatus, the apparatus comprising: a processor configured to (1) determine an initial detection efficiency parameter value for each of a plurality of combinations of incident angle and energy level by simulating a pre-determined number of single-energy photons at each combination of incident angle and energy level; (2) calculate an incident spectrum on each energy-discriminating detector for each of a plurality of combinations of pre-determined scan parameters, energy level, and pre-determined patient attenuation parameters; (3) perform a set of calibration scans using the plurality of combinations of pre-determined scan parameters with a phantom arranged within the CT apparatus, the phantom corresponding to the pre-determined patient attenuation parameters; (4) measure detected counts for each energy window at each energy-discriminating detector for each combination of pre-determined scan parameters and the pre-determined patient attenuation parameters; (5) determine a detection efficiency parameter value corresponding to each energy window of each energy-discriminating detector, each combination of pre-determined scan parameters, and the pre-determined patient attenuation parameters, based on the initial detection efficiency parameter value, the incident spectrum, and the detected counts; and (6) determine the detector angular response calibration look-up table based on the determined detection efficiency parameter values corresponding to each energy window of each energy-discriminating detector, the pre-determined scan parameters, and the pre-determined patient attenuation parameters Turning now to the drawings, FIG. 2 illustrates a sparse spectral CT imaging system that includes fixed, sparse photon-counting detectors and a rotating X-ray source. The source trajectory may be inside or outside the ring defined by the photon-counting detectors.

Figure 3:
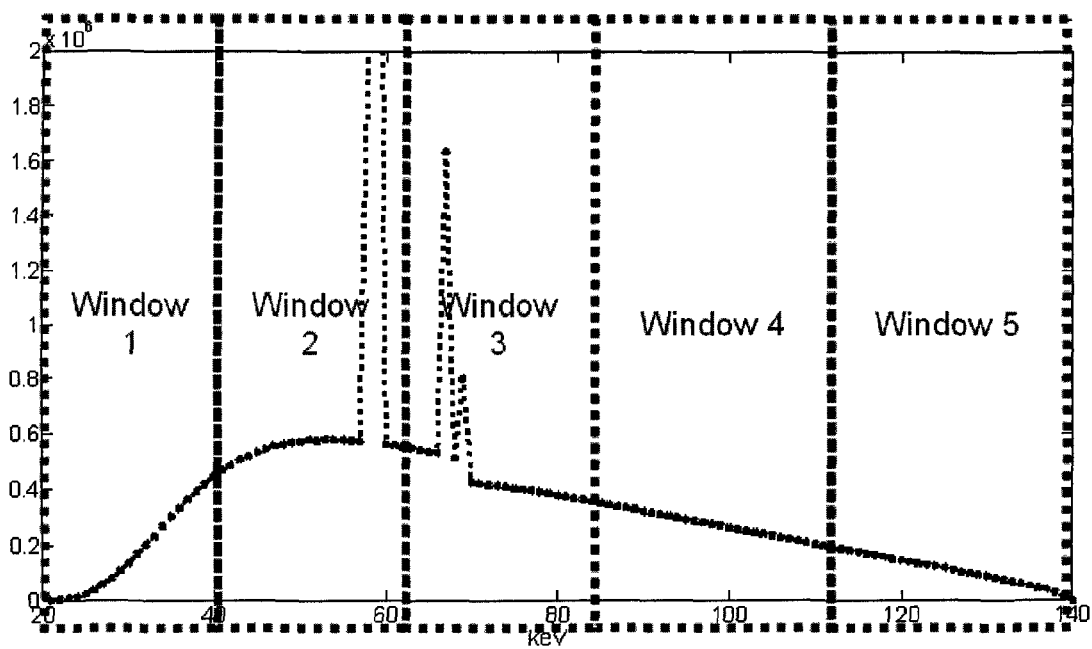
FIG. 3 illustrates an example response of a photon-counting detector in five energy windows.

Photon-counting detectors function by counting X-ray photons in multiple pre-defined, ideally non-overlapping energy windows. FIG. 3 shows an example response of a photon-counting detector in five pre-defined, non-overlapping energy windows.

Figure 4A:
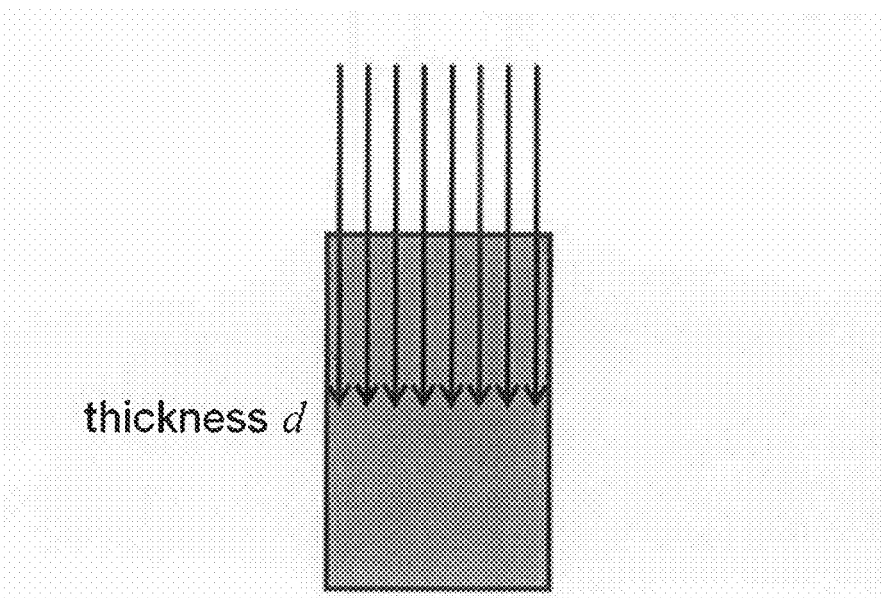
FIGS. 4A and 4B illustrate X-ray beams entering a detector surface.
Figure 4B:
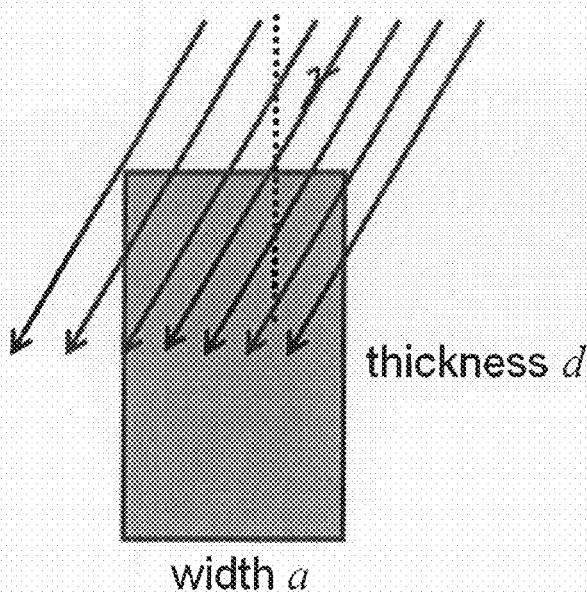

FIGS. 4A and 4B illustrate X-ray beams entering a detector surface. In a current third-generation CT scanner, an incident X-ray beam (neglecting the scattered photons) is perpendicular to the detector surface, as shown in FIG. 4A, and the path length through the detector, l, is constant and equal to the thickness, d, of the detector, regardless of channel and view position. In this case, data acquisition is modeled as $$I_{det} = \int dE S_0(E) D(E) e^{-\int dl \mu(E)}$$

where $I_{det}$ is the detected photon count, E is X-ray photon energy, $S_0(E)$ is incident spectrum before the patient, $\mu(E)$ is the patient linear attenuation coefficient as a function of photon energy E. Further, D(E) is the detector efficiency which is, in this case, simply given by $$D(E) = 1 e^{-\mu_d(E) l} = 1 e^{-\mu_d(E) d}$$

where $\mu_d(E)$ is the linear attenuation coefficient of the detector.

In a sparse, fourth-generation geometry, an X-ray beam may enter the detector surface at an angle $\gamma > 0$, or even from the side, as shown in FIG. 4B. In contrast, in a third-generation geometry, $\gamma = 0$, as shown in FIG. 4A. Accordingly, in a sparse, fourth-generation geometry, $\gamma$ may vary from channel to channel and from view to view. $\gamma$ determines the path length l through the detector. Accordingly, the overall detection efficiency $D(\gamma, E)$ is both angle- and spectra-dependent.

Figure 5A:
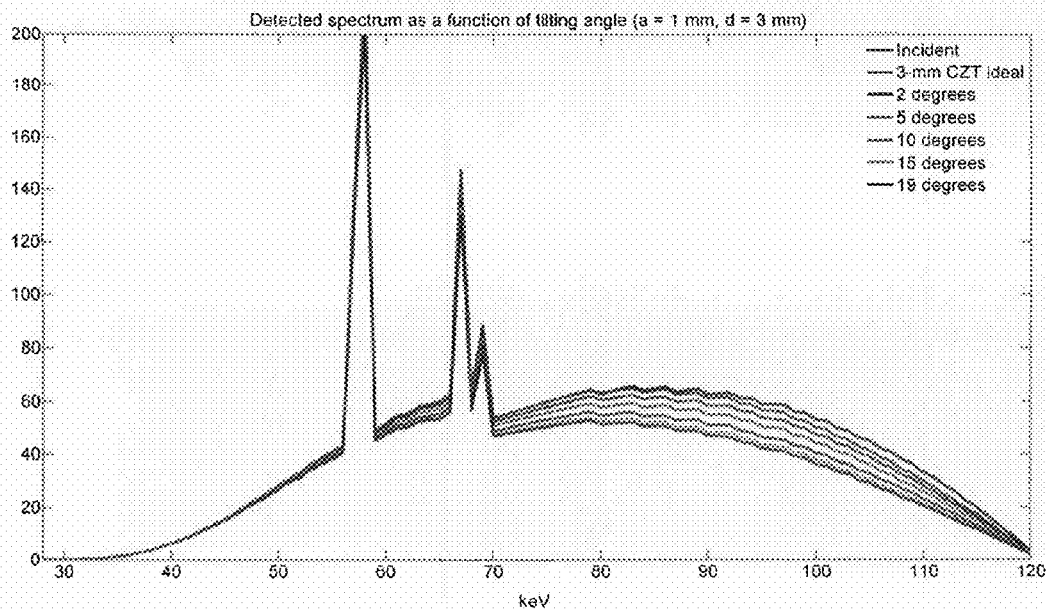
FIGS. 5A and 5B illustrate examples of the angular dependency of detected X-ray spectra of CdZnTe (CZT) detectors.
Figure 5B:
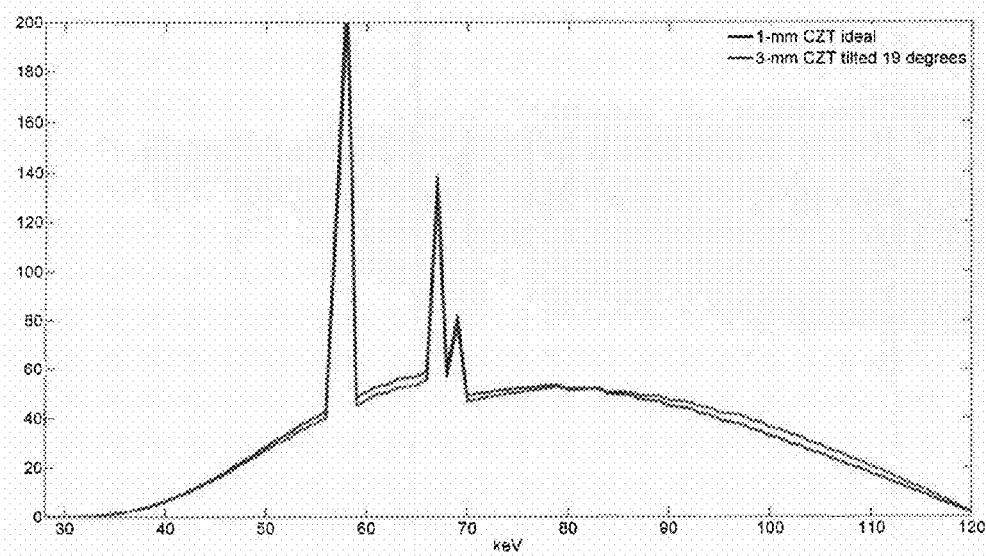

FIGS. 5A and 5B illustrate examples of the angular dependency of detection efficiency of CdZnTe (CZT) detectors. FIG. 5A illustrates an example of the angular dependency of the detected spectra for CZT detectors with different tilting angles. FIG. 5B illustrates an example of the angular dependency of the detected spectra for both an ideal and a tilted CZT detector. As shown in FIG. 5B, at $\gamma = 19°$, a 3-mm CZT detector behaves almost the same as a 1-mm CZT detector at $\gamma = 0°$.

In addition to being angle- and spectra-dependent, $D(\gamma, K)$ may further depend on the count rate. In particular, photon-counting detectors are more prone to such dependency due to a polarization effect. This is because, even with count-loss correction, there may be a residual effect from count-rate dependency, and further because, in a realistic photon-counting detector, the multiple energy windows may not be strictly non-overlapping due to detector energy resolution. If left un-calibrated for, data inconsistency may occur between a calibration scan and a patient scan, resulting in degraded image quality and loss of diagnostic power.

According to one embodiment, there is provided a method to compensate for angular dependency by using Monte Carlo simulation to pre-calculate the angle- and spectra-dependent detection efficiency $D(\gamma, E)$.

According to another embodiment, in addition to Monte Carlo simulation, a calibration scan is implemented to capture any residual count rate dependency and energy resolution blurring of $D(\gamma, E)$.

Figure 6:
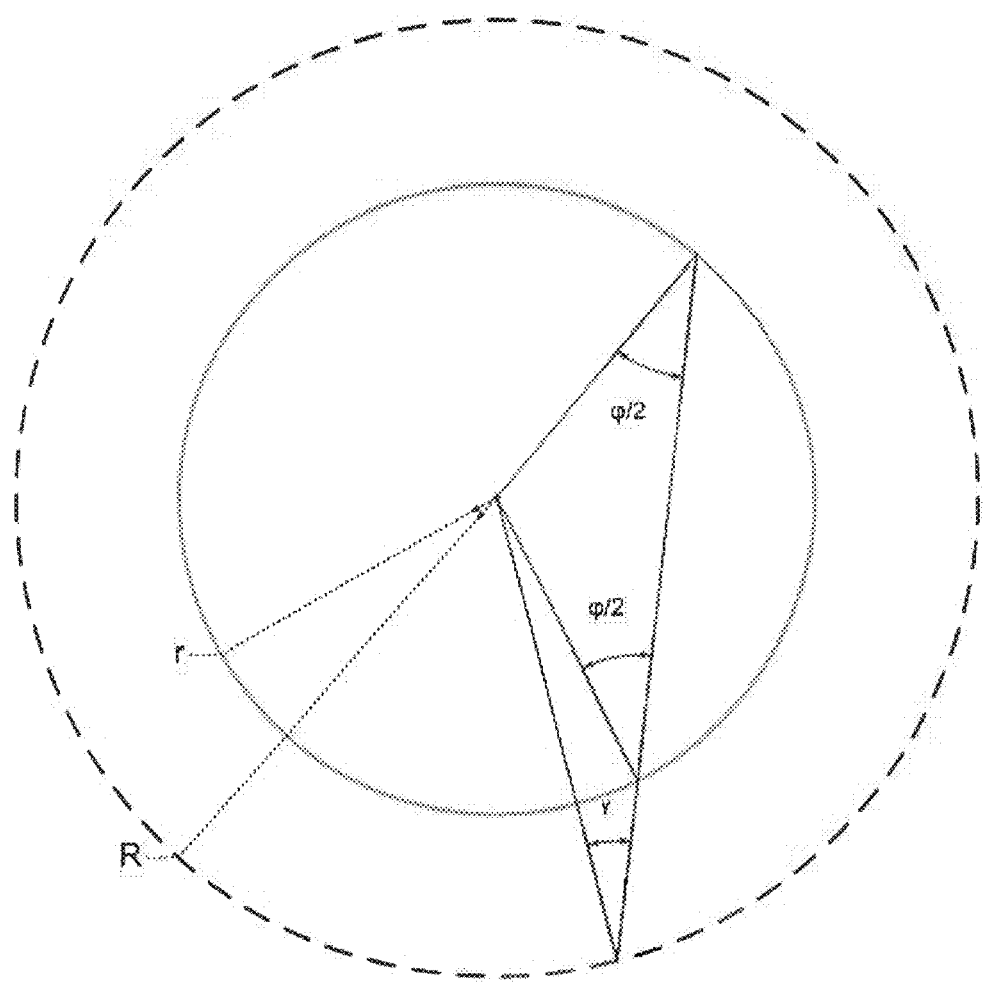
FIG. 6 illustrates relative positions of an X-ray source and a fixed, sparse detector.

According to one embodiment, based on the resulting $D(\gamma, E)$ from the Monte Carlo simulation and the calibration scan, angular dependency is compensated for in sparse spectral CT imaging systems on a view-by-view and channel-by-channel basis. According to this embodiment, during a scan, $\gamma$ is determined by the relative position between the X-ray source and the detector channel of interest as shown in FIG. 6, where R and r are the distances of the detector and the X-ray source, respectively, from the center of the CT imaging system, and $\phi/2$ is the angle between the line that connects the X-ray source with the detector and the line that connects the X-ray source with the center of the CT imaging system. Accordingly, $\gamma$ is given by $$\gamma = \sin^{-1}\left(\frac{r\sin(\phi/2)}{R}\right)$$

In this derivation of γ, parallel beam geometry at the detector is assumed (as shown in FIGS. 4A and 4B), since R and r are large compared with the detector size.

According to one embodiment, Monte Carlo simulation is used to pre-calculate the overall effective detection efficiency at an incident angle γ and photon energy E.

Figure 7:
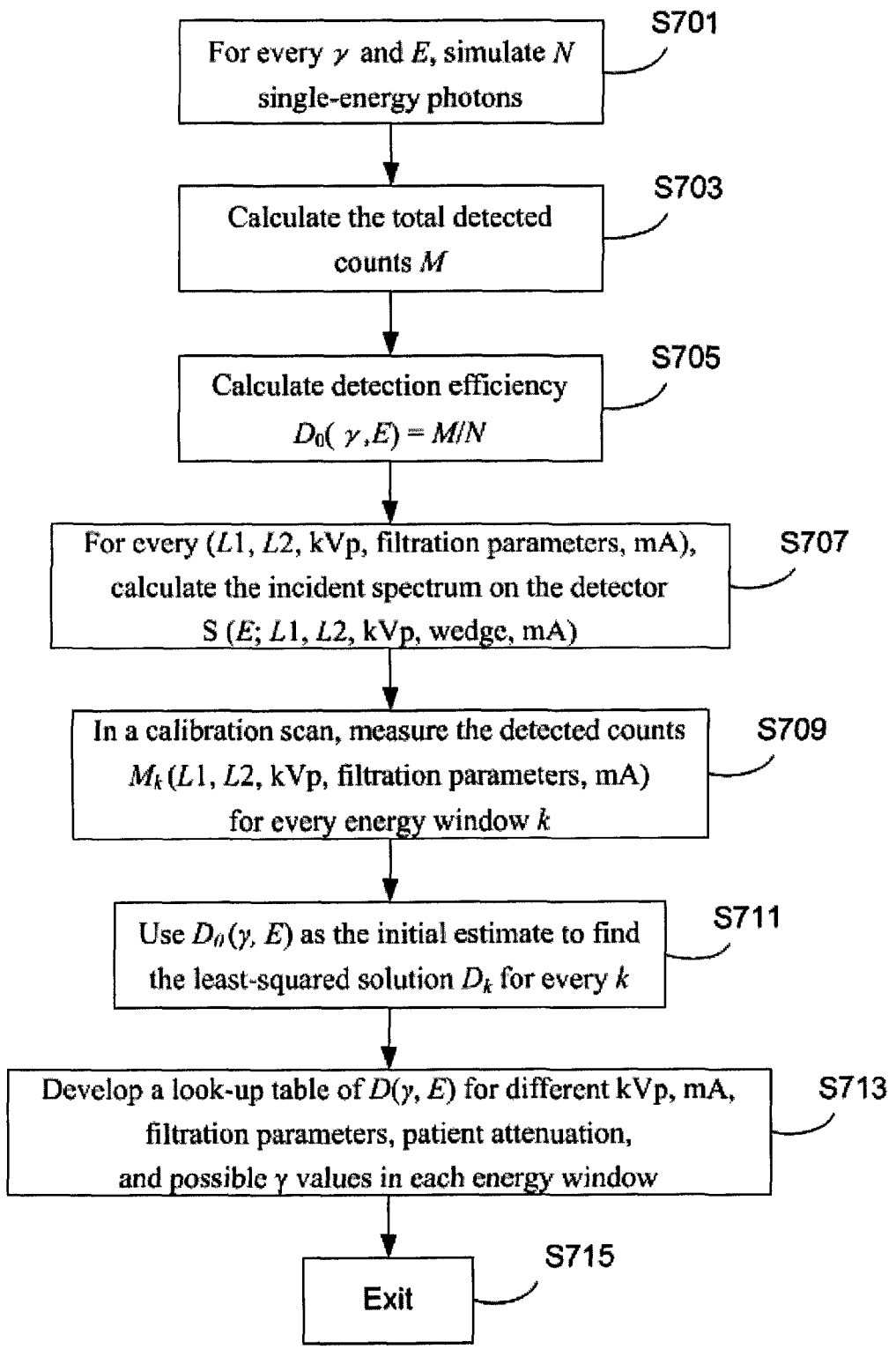
FIG. 7 is a flowchart of a method for determining an angular calibration table for sparse CT imaging systems.

FIG. 7 is a flowchart illustrating a method for determining an angular calibration look-up table for sparse CT imaging systems using Monte Carlo simulation and calibration scans. Monte Carlo simulation is used to provide an initial estimate for the calibration scans. Any standard Monte Carlo package may be used and the simulation results may be pre-calculated for each scanner geometry, e.g., a fourth-generation scanner with sparse, fixed photon-counting detectors, or other geometries containing such detectors.

To pre-calculate the detection efficiency using the Monte Carlo simulation, a large number (N) of single-energy photons, which interact with the detector at the desired incident angle, γ, are generated. Based on the known probability of different photon-matter interacting mechanisms, the event history of each photon (e.g., interact vs. no interact, interact via mechanism A vs. interact via mechanism B) is tracked and recorded. Eventually, the number of photons that do interact with and are detected in the detector is computed as the number M. By definition, M/N yields the detection efficiency of the detector under that given geometry. See steps S701-S705 below.

In step S701, for every γ of interest and for every E of interest, N single-energy photons at energy E and with an incident angle γ on each photon-counting detector are simulated. The detector geometry is assumed to be known.

In step S703, the total detected counts M are calculated from the results of the Monte Carlo simulation.

In step S705, detection efficiency is calculated as:

$$D_0(\gamma, E) = M/N$$

In the next steps, the incident spectrum on the detector is calculated and a set of calibration scans are performed for different values of kVp, mA, filtration parameters, and patient attenuation to compensate for any residual count rate dependency and energy resolution blurring of D(γ, E). Patient attenuation is parametrically described by its basis material decomposition $\{L_1, L_2\}$. The following relationship is estimated and stored in a look-up table for later use:

$$D_k(\gamma, E) = F_k(\gamma, E; L_1, L_2, kVp, \text{filtration parameters}, mA)$$

k=1, ..., # of total energy windows

In step S707, for every combination of (L1, L2, kVp, filtration parameters, mA), the incident spectrum on the detector, S (E; L1, L2, kVp, filtration parameters, mA) is calculated.

According to one embodiment, the incident spectrum on the detector, S (E; L1, L2, kVp, filtration parameters, mA) is calculated analytically using established and proven analytical algorithms.

According to another embodiment, the incident spectrum on the detector, S (E; L1, L2, kVp, filtration parameters, mA) is calculated by a Monte Carlo simulation.

In step S709, a calibration scan is performed, with a phantom arranged with the CT scanner, for every combination of (L1, L2, kVp, filtration parameters, mA), and the detected counts $M_k$ (L1, L2, kVp, filtration parameters, mA) are measured for every energy window k.

In step S711, $D_0$ (γ, E) is used as the initial estimate to find the least-squared solution below for every k $$D_k = \underset{D}{\arg\min}\left(M_k - \int_{E_k}^{E_{k+2}} dE\, S(E) D(\gamma, E)\right)^2$$

where $E_k$ is the $k^{th}$ energy threshold and S(E) includes patient attenuation.

In step S713, the results of the Monte Carlo simulation and the calibration scans are used to develop a look-up table of D(γ, E) for different kVp, mA, filtration parameters, patient attenuation (described by $\{L_1, L_2\}$), and a range of possible γ values in each energy window.

Figure 8:
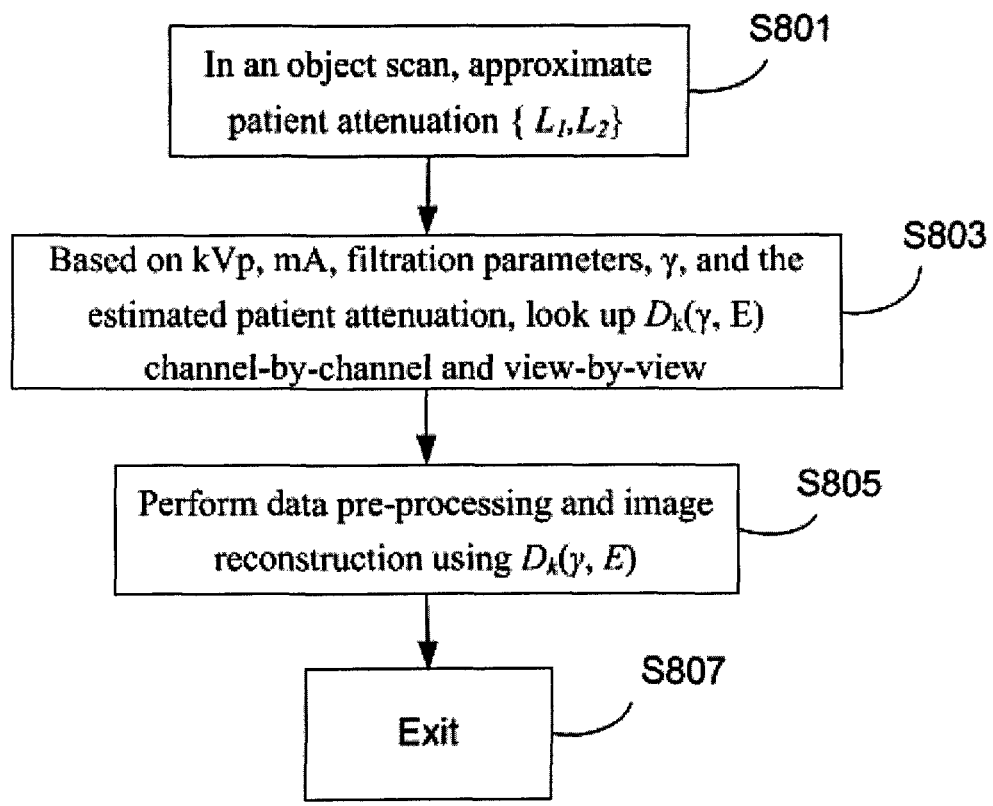
FIG. 8 is a flowchart of a calibration method for sparse CT imaging systems using an angular calibration table.

FIG. 8 is a flowchart of a calibration method for a sparse spectral CT imaging system using an angular calibration table.

In step S801, in an object scan, patient attenuation $\{L_1, L_2\}$ is approximated.

According to one embodiment, patient attenuation is approximated by a first-pass of image reconstruction using the un-corrected D(γ, E).

According to another embodiment, patient attenuation is iteratively approximated by repeating steps S803 and S805 set forth below.

In step S803, based on the applicable kVp, mA, filtration parameters, γ, and the estimated patient attenuation, the corresponding $D_k(\gamma, E)$ is obtained from the look-up table channel-by-channel and view-by-view.

In step S805, data pre-processing and image reconstruction is performed using $D_k(\gamma, E)$ as the effective detection efficiency in the data acquisition model:

$$I_{det,k} = \int_{W_k} dE\, S_0(E) D_k(\gamma, E) e^{-\int dl \mu(E, r)}$$

where k=1, ..., # of total energy windows, and $W_k$ is the $k^{th}$ energy window.

Figure 9:
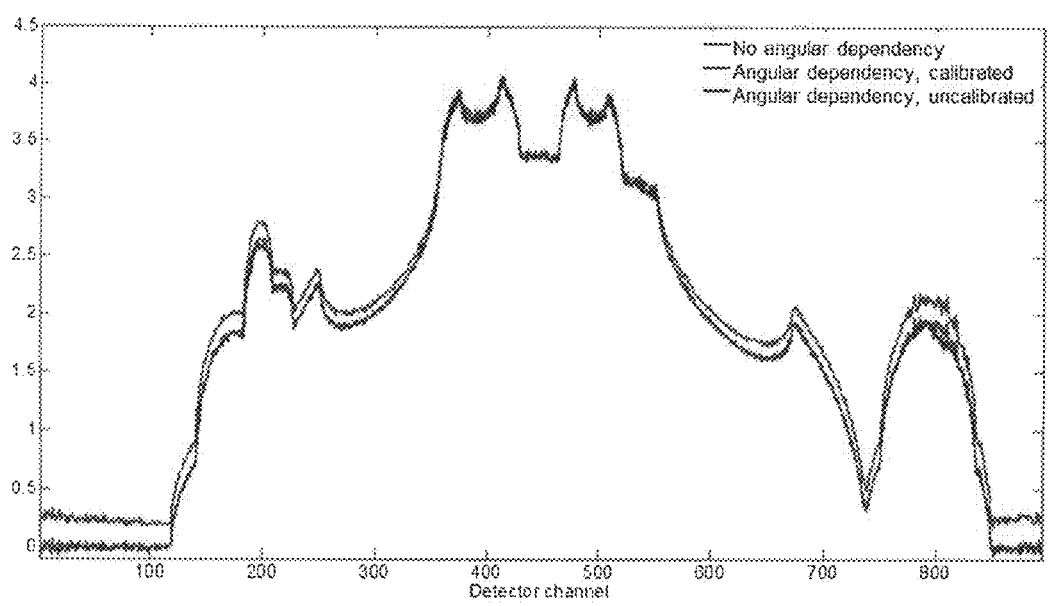
FIG. 9 illustrates the mismatched detector response between various patient and calibration scans with and without the disclosed angular calibration.

FIG. 9 illustrates mismatched detector responses between patient and calibration scans. In FIG. 9, the blue line represents data acquired without angular dependence, so no angular correction is needed; the green line represents data acquisition with angular dependence and the disclosed angular response calibration; and the red line represents data acquired with angular dependence and no angular response calibration. Without angular calibration (blue line vs. red line), there is a significant data error in the projection domain, which will translate into degraded image quality. With angular calibration (blue line vs. green line), the data mismatch is compensated for.

Figure 10:
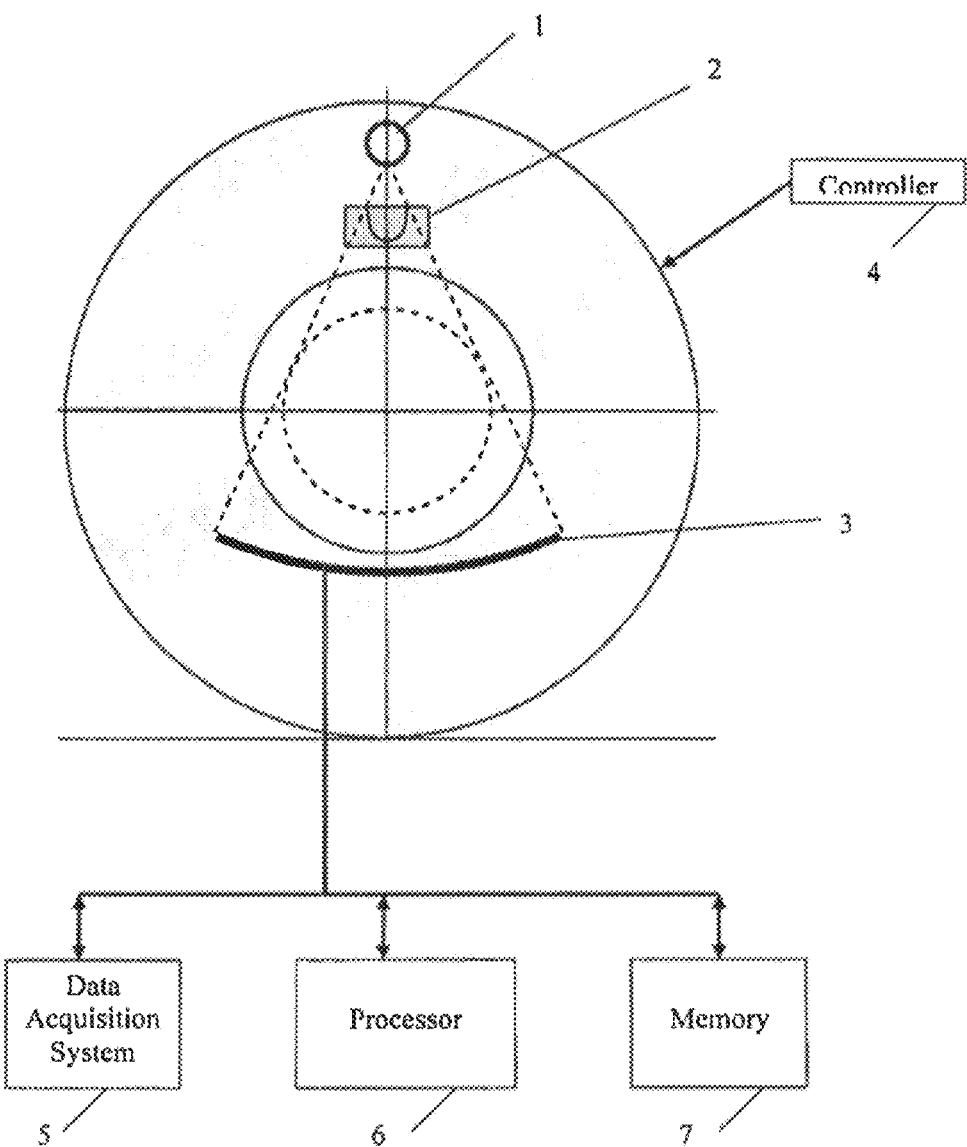
FIG. 10 is a diagram of a mechanically simplified CT apparatus.

FIG. 10 illustrates the basic structure of a CT apparatus that can include the detectors described herein. The CT apparatus of FIG. 10 includes an X-ray tube 1, filters and collimators 2, and detector 3. The CT apparatus will also include additional mechanical and electrical components such as a gantry motor and a controller 4 to control the rotation of the gantry, control the X-ray source, and control a patient bed. The CT apparatus also includes a data acquisition system 5 and a (reconstruction) processor 6 to generate CT images based on the projection data acquired by the data acquisition system. The processor and data acquisition system make use of a memory 7, which is configured to store e.g., data obtained from the detector and reconstructed images.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

The processor 6 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

The disclosed embodiments effectively incorporate the angular dependency of detector detection efficiency into current CT data acquisition models.

The disclosed embodiments compensate for data inconsistency due to the angular dependency of detector response as well as any possible residual effect from count rate dependency and energy resolution blurring.

As would be clear to one of ordinary skill in the art, the above-disclosed methods for detector angular-response calibration apply to all CT scanner geometries, including single-slice and multi-slice scanners. Moreover, the disclosed methods can be used with all CT beam types, including parallel beams, fan-beams, and cone-beams. Further, the above-described methods can also be used with tilted CZT detectors.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for detector angular response calibration in computed-tomography (CT), the method comprising:
    capturing incident X-ray photons, emitted from an X-ray source at a given view using pre-determined scan parameters, via a plurality of energy-discriminating detectors;
    determining photon counts of the captured incident X-ray photons in a plurality of energy windows at each energy-discriminating detector; and
    adjusting the photon counts in each of the plurality of energy windows at each energy-discriminating detector based on a pre-determined detector angular response calibration look-up table.

2. The method of claim 1, wherein the adjusting step comprises:
    estimating patient attenuation parameters based on the determined photon counts;
    obtaining an effective detection efficiency parameter value for the given view in each energy window at each energy-discriminating detector based on the pre-determined detector angular response calibration look-up table, the estimated patient attenuation parameters, and the pre-determined scan parameters; and
    adjusting the photon counts for the given view in each energy window at each energy-discriminating detector based on the obtained effective detection efficiency parameter value.

3. The method of claim 2, wherein the estimating step comprises:
    estimating the patient attenuation parameters by performing a first-pass of image reconstruction based on an uncorrected detection efficiency parameter value.

4. The method of claim 2, wherein the estimating step comprises:
    iteratively approximating the patient attenuation parameters.

5. A computed-tomography (CT) apparatus, comprising:
    a plurality of energy-discriminating detectors configured to capture incident X-ray photons emitted from an X-ray source at a given view using pre-determined scan parameters; and
    a processor configured to
        determine photon counts of the captured incident X-ray photons in a plurality of energy windows at each energy-discriminating detector; and
        adjust the photon counts in each of the plurality of energy windows at each energy-discriminating detector based on a pre-determined detector angular response calibration look-up table.

6. The CT apparatus of claim 5, wherein the processor is further configured to:
    estimate patient attenuation parameters based on the determined photon counts;
    obtain an effective detection efficiency parameter value for the given view in each energy window at each energy-discriminating detector based on the pre-determined detector angular response calibration look-up table, the estimated patient attenuation parameters, and the pre-determined scan parameters; and
    adjust the photon counts for the given view in each energy window at each energy-discriminating detector based on the obtained effective detection efficiency parameter value.

7. The CT apparatus of claim 6, wherein the processor is further configured to:
    estimate the patient attenuation parameters by performing a first-pass of image reconstruction based on an uncorrected detection efficiency.

8. The CT apparatus of claim 6, wherein the estimating step comprises:
    iteratively approximating the patient attenuation parameters.

9. A method to determine a detector angular response calibration look-up table to calibrate angular responses of a plurality of energy-discriminating detectors, each detector having a plurality of energy windows, in a computed-tomography (CT) apparatus, the method comprising:
- determining an initial detection efficiency parameter value for each of a plurality of combinations of incident angle and energy level by simulating a pre-determined number of single-energy photons at each combination of incident angle and energy level;
- calculating an incident spectrum on each energy-discriminating detector for each of a plurality of combinations of pre-determined scan parameters, energy level, and pre-determined patient attenuation parameters;
- performing a set of calibration scans using the plurality of combinations of pre-determined scan parameters with a phantom arranged within the CT apparatus, the phantom corresponding to the pre-determined patient attenuation parameters;
- measuring detected counts for each energy window at each energy-discriminating detector for each combination of pre-determined scan parameters and the pre-determined patient attenuation parameters;
- determining a detection efficiency parameter value corresponding to each energy window of each energy-discriminating detector, each combination of pre-determined scan parameters, and the pre-determined patient attenuation parameters, based on the initial detection efficiency parameter value, the incident spectrum, and the detected counts; and
- determining the detector angular response calibration look-up table based on the determined detection efficiency parameter values corresponding to each energy window of each energy-discriminating detector, the pre-determined scan parameters, and the pre-determined patient attenuation parameters.

10. The method of claim 9, wherein the step of determining the initial detection efficiency comprises:
- simulating the pre-determined number of single-energy photons at each combination of energy level and incident angle;
- calculating a total detected count of incident X-ray photons at each energy-discriminating detector based on the simulated pre-determined number of single-energy photons; and
- calculating the initial detection efficiency parameter value for each of the plurality of combinations of incident angle and energy level, based on the pre-determined number of single-energy photons and the calculated total detected count.

11. An apparatus to determine a detector angular response calibration look-up table to calibrate angular responses of a plurality of energy-discriminating detectors, each detector having a plurality of energy windows, in a computed-tomography (CT) apparatus, the apparatus comprising:
- a processor configured to
  - determine an initial detection efficiency parameter value for each of a plurality of combinations of incident angle and energy level by simulating a pre-determined number of single-energy photons at each combination of incident angle and energy level;
  - calculate an incident spectrum on each energy-discriminating detector for each of a plurality of combinations of pre-determined scan parameters, energy level, and pre-determined patient attenuation parameters;
  - perform a set of calibration scans using the plurality of combinations of pre-determined scan parameters with a phantom arranged within the CT apparatus, the phantom corresponding to the pre-determined patient attenuation parameters;
  - measure detected counts for each energy window at each energy-discriminating detector for each combination of pre-determined scan parameters and the pre-determined patient attenuation parameters;
  - determine a detection efficiency parameter value corresponding to each energy window of each energy-discriminating detector, each combination of pre-determined scan parameters, and the pre-determined patient attenuation parameters, based on the initial detection efficiency parameter value, the incident spectrum, and the detected counts; and
  - determine the detector angular response calibration look-up table based on the determined detection efficiency parameter values corresponding to each energy window of each energy-discriminating detector, the pre-determined scan parameters, and the pre-determined patient attenuation parameters.

12. The apparatus of claim 11, wherein, in determining the initial detection efficiency, the processor is further configured to:
- simulate the pre-determined number of single-energy photons at each combination of energy level and incident angle;
- calculate a total detected count of incident X-ray photons at each energy-discriminating detector based on the simulated pre-determined number of single-energy photons; and
- calculate the initial detection efficiency parameter value for each of the plurality of combinations of incident angle and energy level, based on the pre-determined number of single-energy photons and the calculated total detected count

* * * * *